(12) United States Patent
Kim et al.

(10) Patent No.: US 10,506,973 B2
(45) Date of Patent: Dec. 17, 2019

(54) APPARATUS FOR INJECTING LIQUID INTO PRIMO-NODE AND PRIMO-VASCULAR SYSTEM TRACING SYSTEM COMPRISING THE SAME

(71) Applicants: Samsung Electronics Co., Ltd., Suwon-si, Gyeonggi-do (KR); AICT (Advanced Institutes of Convergence Technology), Suwon-si, Gyeonggi-do (KR)

(72) Inventors: Minseoks Kim, Yongin-si (KR); Seunghwan Lee, Daejeon (KR); Kwangsup Soh, Gwacheon-si (KR); Hyunseok Jang, Gangwon-do (KR); Sharon Jiyoon Jung, Goyang-si (KR); Youngjun Koh, Yongin-si (KR); Jaeyoung Kim, Seoul (KR)

(73) Assignees: SAMSUNG ELECTRONICS CO., LTD., Suwon-si (KR); AICT (ADVANCED INSTITUTES OF CONVERGENCE TECHNOLOGY), Suwon-si (KR)

( * ) Notice: Subject to any disclaimer, the term of this patent is extended or adjusted under 35 U.S.C. 154(b) by 1057 days.

(21) Appl. No.: 14/945,172

(22) Filed: Nov. 18, 2015

(65) Prior Publication Data
US 2016/0136046 A1    May 19, 2016

(30) Foreign Application Priority Data
Nov. 18, 2014 (KR) .................... 10-2014-0160880

(51) Int. Cl.
*A61M 1/00* (2006.01)
*A61M 5/32* (2006.01)
(Continued)

(52) U.S. Cl.
CPC .......... *A61B 5/4854* (2013.01); *A61M 5/007* (2013.01)

(58) Field of Classification Search
CPC ............ A61B 2017/306; A61M 1/106; A61M 2025/0039; A61M 2025/0089; A61M 25/06
See application file for complete search history.

(56) References Cited

U.S. PATENT DOCUMENTS

| | | | |
|---|---|---|---|
| 7,842,015 B2 | 11/2010 | Chachques et al. | |
| 7,855,067 B2 | 12/2010 | Sasaki et al. | |
| 2003/0114796 A1* | 6/2003 | Schmidt | A61B 17/3478 604/158 |

FOREIGN PATENT DOCUMENTS

| | | |
|---|---|---|
| KR | 2012-0129056 A | 11/2012 |
| KR | 2013-0094425 A | 8/2013 |
| KR | 2013-0137930 A | 12/2013 |

* cited by examiner

*Primary Examiner* — Rebecca E Eisenberg
(74) *Attorney, Agent, or Firm* — Leydig, Voit & Mayer, Ltd.

(57) ABSTRACT

Provided are an apparatus for injecting a liquid into a primo-node and a primo-vascular system tracing system including the apparatus. The apparatus includes a liquid injection tube to inject a liquid into a primo-node of an object, and a suction tube to hold the primo-node to inject the liquid injection tube into the primo-node. The liquid injection tube and the suction tube are formed as one body. The liquid injection tube is inserted into an inner side of the suction tube and an edge unit of the liquid injection tube protrudes to the outside from an inner side of a suction opening of the suction tube.

13 Claims, 3 Drawing Sheets

(51) Int. Cl.
*A61B 5/00* (2006.01)
*A61M 5/00* (2006.01)

APPARATUS FOR INJECTING LIQUID INTO PRIMO-NODE AND PRIMO-VASCULAR SYSTEM TRACING SYSTEM COMPRISING THE SAME

RELATED APPLICATION

This application claims the benefit of Korean Patent Application No. 10-2014-0160880, filed on Nov. 18, 2014, in the Korean Intellectual Property Office, the disclosure of which is incorporated herein in its entirety by reference.

BACKGROUND

1. Field

The present disclosure relates to an apparatus for injecting a liquid into a primo-node and a primo-node tracing system comprising the same.

2. Description of the Related Art

The primo-vascular system (PVS), which was disclosed in the early 1960s, includes primo-nodes (PNs) and primo-vessels (PVs). A PN is a circulatory system distinguished from a blood vessel, a lymph vessel, and the nervous system. It is known that a portion of the PVS has a thread structure in a blood vessel. As a result of many PVS studies, it have been determined that the PVS exists in blood vessels, nervous tissues, surfaces of internal organs, outer surface of many organs, and lymph vessels.

A PN is a small and soft tissue surrounded by a relatively tough and thin film. A PN, and movement thereof, may be observed by injecting a predetermined dye material into the PN. However, the continuous observation of the PN is not easy as the PN does not remain in a fixed state and its shape and position may change. Thus, it is necessary to identify new apparatuses and methods to observe PNs. This invention provides such an apparatus.

SUMMARY

Provided is an apparatus for injecting a liquid into a primo-node.

Provided is a primo-vascular system (PVS) tracing system for detecting and tracing a primo-node after injecting a liquid thereinto.

In one embodiment, provided is an apparatus for injecting a liquid into a primo-node, the apparatus comprising a liquid injection tube that injects a liquid into a primo-node of an object positioned within a suction tube that holds the primo-node while the liquid injection tube inserted therein.

In another embodiment, provided is a primo-vascular system (PVS) tracing system comprising an injector that injects a liquid into an object; and an image taker that takes an image of the object; wherein the injector comprises a liquid injection tube that inject a liquid positioned within a suction tube that holds the primo-node while the liquid injection tube inserted therein.

Also provided A method of injecting liquid into a primo-node, the method comprising contacting a primo node with an apparatus of claim 1, wherein the liquid injection tube penetrates the primo node; applying a suction to the primo node through the suction tube, whereby the suction holds the primo node to the suction tube; and injecting liquid into the primo node through the liquid injection tube while applying suction to the primo node through the suction tube.

Additional aspects will be set forth in part in the description which follows and, in part, will be apparent from the description, or may be learned by practice of the presented exemplary embodiments.

According to an aspect of an exemplary embodiment, an apparatus for injecting a liquid into a prime-node, the apparatus comprising: a liquid injection tube to inject a liquid into a primo-node of an object; and a suction tube to hold the primo-node in a state with the liquid injection tube inserted therein.

The liquid injection tube and the suction tube may be joined as one body or part.

The liquid injection tube may be inserted into an inner side of the suction tube, and an edge unit of the liquid injection tube protrudes to the outside from an inner side of a suction opening of the suction tube.

The liquid injection tube may have an outer diameter smaller than an inner diameter of the suction tube.

The liquid injection apparatus may further include a bridge or housing to fix the liquid injection tube to the suction tube. The bridge or housing may further provide a pathway fluidly connecting the suction tube to a negative pressure source (pump).

The liquid injection apparatus may further include a suction pipeline (e.g., tube) connected to a side of the bridge and a negative pressure pump connected to the suction pipeline.

The suction tube may be adhered onto a surface of a primo-node by using negative pressure.

According to an aspect of an exemplary embodiment, a primo-vascular system tracing system includes: an injector to inject a liquid into an object; and an image taker to observe the object and take an image of the object, wherein the injector comprises: a liquid injection tube to inject a liquid into a primo-node of an object; and a suction tube to hold the primo-node in a state with the liquid injection tube inserted therein.

The injector may include: a height controller; a micro manipulator mounted on an edge of the height controller; and a liquid injection apparatus mounted on the micro manipulator.

A weight center of the micro manipulator may be coupled to the height controller.

The micro manipulator may further include an extension unit, wherein the liquid injection apparatus is mounted on the extension unit.

The primo-vascular system tracing system may further include a display to display an image taken by the image taker; and a controller.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
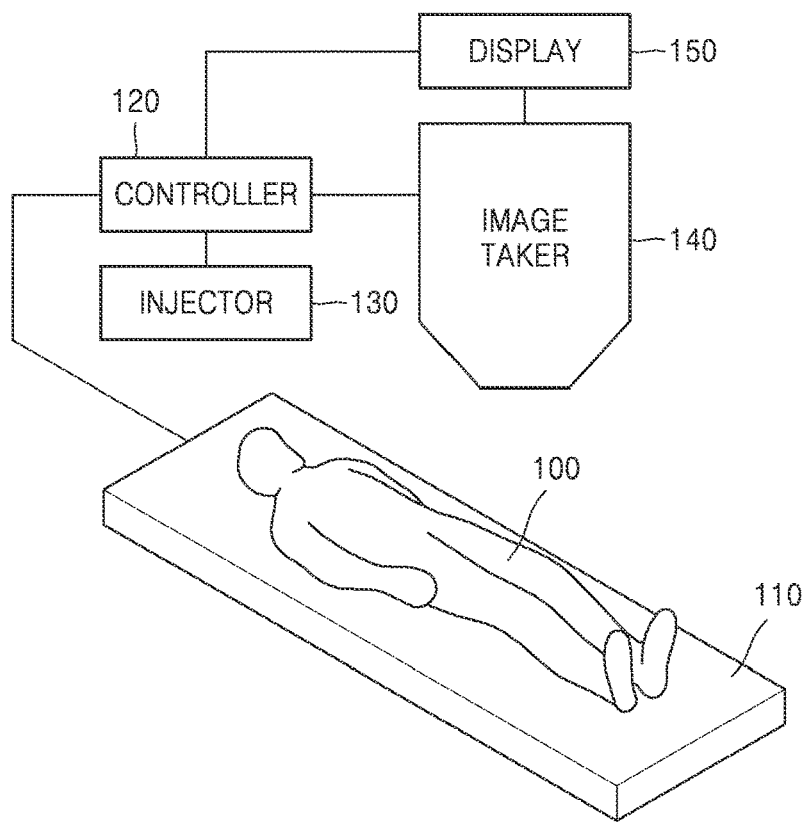
FIG. 1 is a schematic drawing illustrating a primo-vascular system tracing system according to an embodiment of the inventive concept.

A liquid injection apparatus and a primo-vascular system tracing system according to an embodiment of the inventive concept will now be made in detail to exemplary embodiments, examples of which are illustrated in the accompanying drawings. In the drawings, like reference numerals refer to like elements throughout and elements having the same reference numerals may be formed of the same material. Also, the widths and thicknesses of layers and regions are exaggerated for clarity.

FIG. 1 is a schematic drawing of a primo-vascular system tracing system according to an embodiment of the inventive concept.

Referring to FIG. 1, the primo-vascular system tracing system according to an exemplary embodiment may include a table 110 on which an object 100 under examination is positioned, an injector 130 that injects a liquid into the object 100, and a display 150 that displays an image taken by an image taker 140. The table 110, the injector 130, the image taker 140, and the display 150 may be controlled by a controller 120.

The object 100 may be a human, an animal, a portion of a human, or a portion of an animal. For example, the object 100 may be an organ, such as heart, brain, womb, breast, or abdomen, a spinal code, or a blood vessel. After the object 100 is positioned on the table 110, the object 100 may be moved in various directions by moving the table, for example, in at least one of up, down, left, and right directions relative to the injector 130 (e.g., towards, away from, or laterally with respect to the injector). Also, the table 110 may be able to tilt at a predetermined angle or to rotate in a predetermined direction relative to the injector 130. The table 110 may include a heating pad or a temperature control device.

The image taker 140 may include an illumination device, a microscope, and a camera. The image taker 140 may include an illumination system having a light-emitting device that may irradiate light onto at least a portion of the object 100. The light-emitting device is not specifically limited. The microscope is disposed in a position allowing observation of the object 100 or a portion of the object 100 located on the table 110 by magnifying it, and may be a tissue microscope, a phase-contrast microscope, or a stereoscopic microscope. The image taker 140 may take a picture of a portion or the entire object 100 that is positioned on the table 110, and may include a charge-coupled device (CCD). The image taker 140 may be mounted on a microscope and take a picture of a microscopic image. The image taker 140 may further include an illumination device to observe at least a portion of the object 100. The illumination device may be a halogen lamp or an optical fiber. The display 150 may display an image taken by the image taker 140 to be visually observed by a user.

The injector 130 injects a liquid into the object 100 and may include an apparatus for injecting a liquid into a primo-node of the object 100. The injector 130 may include a syringe, a liquid injection tube 21 (refer to FIG. 3) that is attached to an edge of the syringe to directly inject a liquid by being inserted into the object 100, and a suction tube 210 (refer to FIG. 3) that maintains the position of the liquid injection tube inserted into the object 100 when stably attached to the object 100. The injector 130 will be further described in detail below.

The controller 120 may control the position of the table 110 on which the object 100 is seated, and also, may control the heating pad and the temperature control device that are attached to the table 110. The controller 120 may also control the operation of the image taker 140 and the display 150, and also, may control an injection velocity and amount of the liquid injecting into the object 100.

Figure 2:
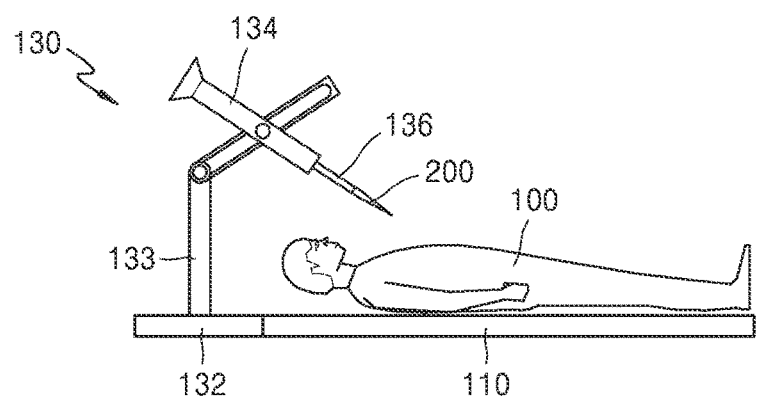
FIG. 2 is a schematic drawing illustrating an injector of a primo-vascular system tracing system according to an embodiment of the inventive concept.

FIG. 2 is a schematic drawing of the injector 130 of a primo-vascular system tracing system according to an embodiment of the inventive concept.

Referring to FIG. 2, the injector 130 may be located on a lateral of the table 110 on which the object 100 is seated, and thus, may inject a liquid into a predetermined region of the object 100, for example, a primo-node of a primo-vascular system. The injector 130 may include a height controller 133 that is formed on a stand 132, and a micro manipulator 134 may be mounted on an edge of the height controller 133. The micro manipulator 134 may precisely control the position of a liquid injection apparatus 200 that injects various specimen or contrast media into a primo-node of the object 100, and the liquid injection apparatus 200 may be mounted on an edge of the micro manipulator 134. The positions of the liquid injection tube 21 (refer to FIG. 3) and the suction tube 210 (refer to FIG. 3) that are formed on an edge of the liquid injection apparatus 200 may be controlled at a micrometer unit by the micro manipulator 134.

If the end of the micro manipulator 134 on which the liquid injection apparatus 200 is mounted is excessively heavy, the control of the liquid injection apparatus 200 may be difficult. Also, when the liquid injection apparatus 200 is used for a long period of time, the end of the micro manipulator 134 on which the liquid injection apparatus 200 is mounted may move downward due to gravity, and thus, the movement of the liquid injection apparatus 200 in a direction that is not desired by the user may occur. Accordingly, in the primo-vascular system tracing system according to the current embodiment, the weight center of the micro manipulator 134 may be coupled to the height controller 133 so that the center of gravity of the micro manipulator 134 of the injector 130 is not biased towards the end of the micro manipulator 134 on which the liquid injection apparatus 200 is mounted.

The amount of liquid injected into the primo-node of the object 100 may be optionally controlled. The injection amount of a liquid may be controlled in a micro-liter unit, such as µl/min, and a long period of injection, for example, an hour or more, may be possible. The liquid injection apparatus 200 may be directly connected to the end of the micro manipulator 134, and the micro manipulator 134 may include an extension unit 136 that extends from the micro manipulator 134. Thus, the liquid injection apparatus 200 may be formed on the extension unit 136 of the micro manipulator 134.

Figure 3:
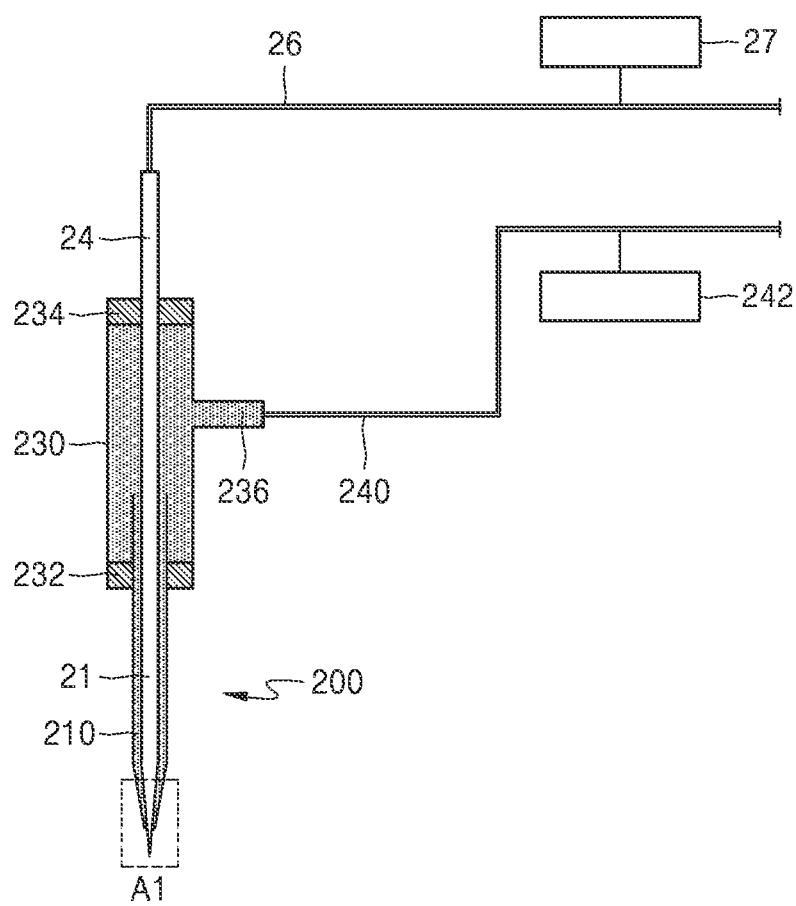
FIG. 3 is a schematic drawing illustrating an apparatus for injecting a liquid into a primo-node, according to an embodiment of the inventive concept.
Figure 4:
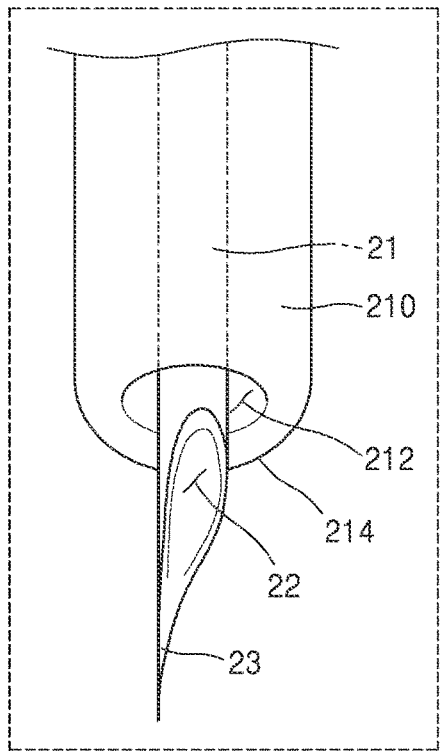
FIG. 4 is a magnified view illustrating a region A1 of FIG. 3.

FIGS. 3 and 4 are schematic drawings of a liquid injection apparatus that inject a liquid into a primo-node according to an embodiment of the inventive concept.

Referring to FIGS. 1 through 3, the injector 130 may include the liquid injection apparatus 200 that injects a liquid into a primo-node of the object 100. The liquid injection apparatus 200 according to the current embodiment may perform as a liquid supply unit for supplying a predetermined liquid that is injected into the object 100 or a primo-node of the object 100. The location of the primo-node may be changed from time to time with the rhythm of physiological action of the object 100, for example, breathing, heart beating, flow of blood, or movement of organs. The liquid injection apparatus 200 according to the current embodiment may perform as a primo-node holder that stably holds the primo-node.

The liquid injection apparatus 200 may include the liquid injection tube 21 through which a liquid may be injected into a primo-node of the object 100 penetrating through the skin of the object 100 (FIG. 2). Also, the liquid injection apparatus 200 may include the suction tube 210 that is positioned around the liquid injection tube 21. In other words, the liquid injection tube 21 is positioned within the suction tube 210, with the circular cross sections concentric or off-set. A hollow space within the liquid injection tube provides a pathway for fluid flow, and a hollow space within the suction tube and between the wall of the suction tube and the wall of the injection tube (e.g., surrounding part or all of the injection tube) provides an airway through which negative pressure (suction) can be applied. When a suction is applied through the suction tube to an object, the liquid injection tube 21 stably injects a liquid into a primo-node in the object 100 penetrating through the skin of the object 100 (see, e.g., FIG. 5). The liquid injection tube 21 and the suction tube 210 may be separately formed, and as depicted in FIG. 2, the liquid injection tube 21 and the suction tube 210 may be joined as one-body. The liquid injection tube 21 may be connected to an injection line 26 through a connection unit 24 and positioned such that the liquid injection tube 21 is within the suction tube 210. Various kinds of liquids, for example, dyes, contrast media, or a liquid that includes fluorescent nano particles may be supplied through the injection line 26. The liquid injection tube 21 may inject various kinds of liquids supplied through the injection line 26 into the object 100 or a primo-node of the object 100. The injection line 26 may be connected to a pump 27.

The suction tube 210 may be fixed to the injection tube 21 through a bridge 230 so that the liquid injection tube 21 is within suction tube 210. Sealants may be formed on the edges or ends 232 and 234 of the bridge 230 to seal the bridge against the suction tube 210 and the liquid injection tube 21 respectively. A lateral unit 236 of the bridge 230 may be connected to a suction pipeline 240, and may provide a fluid connection between the suction pipeline 236 and suction tube 210 via the bridge 230. The suction pipeline 240 may be connected to a negative pressure pump 242 that generates a negative pressure by sucking air. The suction tube 210 may be attached to a surface of a primo-node in a state that allows the liquid injection tube 21 to remain inserted in the primo-node of the object 100. A negative pressure may be applied to the suction tube 210 through the negative pressure pump 242 that is connected to the suction pipeline 240 so that the suction tube 210 is stably attached to a primo-node. The end of the liquid injection tube 21 extends beyond and protrudes from within the suction tube 210, so that the liquid injection tube 21 penetrates into the primo node when the suction tube 210 is attached to the primo node. Since the primo-node continuously moves by a physiological action, such as heart beating of the object 100, the primo-node may be easily held by applying a negative pressure to the suction tube 210 by using the suction pipeline 240 while the suction pipeline 240 is in contact with a surface of the primo-node.

The edge of the end of the liquid injection tube 21 and the suction tube 210 are described with reference to FIG. 4. FIG. 4 is a magnified view of a region A1 of the liquid injection apparatus 200 of FIG. 3.

Referring to FIG. 4, the liquid injection tube 21 may be formed of glass, coated carbon nanotube or plastic material, for example, acrylic. And the suction tube 210 may be formed glass, stainless steel or plastic material, for example, acrylic. An edge 23 of the liquid injection tube 21 may be formed as a sharp edge and/or point that can penetrate into the primo node so that a liquid can be injected into a primo-node in the object 100 through the skin of the object 100. The liquid injection tube 21 may be formed to have a capillary shape with an inner area 22 that is hollow, and may have an inner diameter of a few millimeters or less. For example, a diameter of the capillary of the inner area 22 of the liquid injection tube 21 may be approximately 1~100 micrometers. If the liquid injection tube 21 is formed of coated carbon nanotube, a diameter of the capillary of the inner area 22 of the liquid injection tube 21 may be 1~10 micrometers. The external diameter of the liquid injection tube 21 may be a few micrometers~1000 micrometers, for example 10~30 micrometers. The suction tube 210 may surround the liquid injection tube 21, and may have an inner diameter greater than an external diameter of the liquid injection tube 21. The suction tube 210 may have an inner diameter of, for example, approximately 30~1000 micrometers.

The edge unit 23 of the liquid injection tube 21 may be processed in various shapes, for example, the inner diameter of the edge unit 23 of the liquid injection tube 21 may be formed to have 1 mm or less, for example, may be reduced to a few tens or a few hundred micrometers through fire polishing or mechanical fabrication processing. The edge unit 23 of the liquid injection tube 21 may be bent in a desired direction. In order to process the edge unit 23 of the liquid injection tube 21, a microscope may be used. As depicted in FIG. 4, if the liquid injection tube 21 and the suction tube 210 are formed or joined as one piece, and the edge unit 23 of the liquid injection tube 21 may be formed to protrude beyond the suction opening 212 of the suction tube 210.

Figure 5:
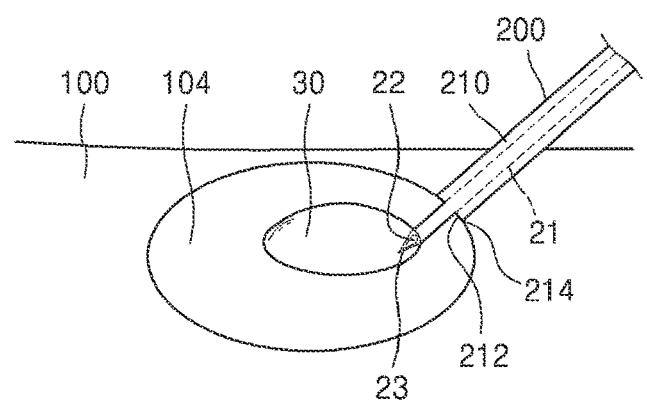
FIG. 5 is a schematic drawing illustrating a method of injecting a liquid into a primo-node by using an apparatus according to an embodiment of the inventive concept.

FIG. 5 is a schematic drawing illustrating a method of injecting a liquid 30 into a primo-node 104 by using a liquid injection apparatus 200 according to an embodiment of the inventive concept.

According to the current exemplary embodiment of FIG. 5, when the liquid 30 is injected into the primo-node 104 of the object 100 through the liquid injection tube 21 of the liquid injection apparatus 200, the edge 23 of the liquid injection tube 21 may be inserted to penetrate through a surface of the primo-node 104. Also, in a state where an edge 214 of the suction tube 210 is in contact with the surface of the primo-node 104, a negative pressure is applied to the suction opening 212 of the suction tube 210 by the negative pressure pump 242 shown in FIG. 3 through the suction opening 212 of the suction tube 210. When the edge unit 214 of the suction tube 210 is in contact with the primo-node 104, the suction tube 210 may hold the primo-node 104 by the negative pressure that is applied to the suction opening 212 of the suction tube 210. When the edge unit 23 of the liquid injection tube 21 is inserted into the primo-node 104 and the suction tube 210 holds the primo-node 104, the liquid 30 may be injected into the primo-node 104 through the internal space 22 of the liquid injection tube 21.

In order to trace the location of the primo-node 104, fluorescent nanoparticles (FNP) may be included in the liquid 30 that is injected into the primo-node 104 through the liquid injection tube 21. The FNP may be formed by coating a material that is stable and harmless to a body, for example, silica $SiO_2$, on nanoparticles together with a dye that emits fluorescence. For example, the FNP may be formed by coating amorphous silica that contains rhodamine bisothiocyanate which is a dye that emits fluorescence on cobalt ferric magnetic nanoparticles, and a poly ethylene glycol (PEG) film that is harmless to a body may be coated on the outermost surface of the nanoparticles. The nanoparticles may have a size of approximately 50 nm, may have a maximum emitting-wavelength of approximately 555 nm, and may have an orange-color fluorescence wavelength. After injecting the liquid 30 containing the FNP into the primo-node 104, the primo-node 104 is observed by using an optical microscope of the image taker 140 shown in FIG. 1 and the image is photographed by using a camera, and thus, the success or failure of the injection of a dye into the primo-node 104 and the moving path of the dye may be readily observed.

According to the current embodiment, a liquid injection apparatus that can inject a liquid into a primo-node by readily holding the primo-node that flows along a physiological phenomenon of a body may be provided.

The current embodiment may also provide a primo-vascular system tracing system by which a desired amount of liquid may be injected into a primo-node of an object over the course of many hours, and the flow of the liquid injected into the primo-node may be readily observed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus for injecting a liquid into a primo-node, the apparatus comprising:
    a suction tube comprising a suction opening formed therein and configured to hold the primo-node;
    a liquid injection tube disposed within the suction tube, wherein an edge of the liquid injection tube protrudes outward from the suction opening; and
    a bridge that fixes the liquid injection tube to the suction tube.

2. The apparatus of claim 1, wherein the liquid injection tube has an outer diameter smaller than an inner diameter of the suction tube.

3. The apparatus of claim 1, further comprising a suction pipeline connected to a side of the bridge.

4. The apparatus of claim 3, further comprising a negative pressure pump connected to the suction pipeline.

5. A primo-vascular system (PVS) tracing system comprising:
    the injector of claim 1 that injects a liquid into a primo node of an object; and
    an image taker that takes an image of the object.

6. The primo-vascular system tracing system of claim 5, wherein the injector comprises:
    a height controller; and
    a micro manipulator mounted on an edge of the height controller;
    and wherein the liquid injector is mounted on the micro manipulator.

7. The primo-vascular system tracing system of claim 6, wherein a weight center of the micro manipulator is coupled to the height controller.

8. The primo-vascular system tracing system of claim 6, wherein the micro manipulator further comprises an extension unit, wherein the liquid injection apparatus is mounted on the extension unit.

9. The primo-vascular system tracing system of claim 6, further comprising:
    a display to display an image taken by the image taker; and
    a controller.

10. A method of injecting liquid into a primo-node, the method comprising
    contacting a primo node with an apparatus of claim 1, wherein the liquid injection tube penetrates the primo node;
    applying a suction to the primo node through the suction tube, whereby the suction holds the primo node to the suction tube; and
    injecting liquid into the primo node through the liquid injection tube while applying suction to the primo node through the suction tube.

11. The method of claim 10, wherein the liquid injection tube of the apparatus has an outer diameter smaller than an inner diameter of the suction tube.

12. The method of claim 10, wherein the apparatus further comprises a suction pipeline connected to a side of the bridge.

13. The method of claim 12, wherein the apparatus further comprises a negative pressure pump connected to the suction pipeline.

* * * * *